US009999546B2

(12) United States Patent
Gardner et al.

(10) Patent No.: US 9,999,546 B2
(45) Date of Patent: Jun. 19, 2018

(54) PROTECTIVE HEADWEAR WITH AIRFLOW

(71) Applicant: ILLINOIS TOOL WORKS INC., Glenview, IL (US)

(72) Inventors: William P. Gardner, Appleton, WI (US); Nishank R. Patel, Appleton, WI (US); Eric T. Sommers, Appleton, WI (US); John C. Mehnert, Madison, WI (US)

(73) Assignee: Illinois Tool Works Inc., Glenview, IL (US)

( * ) Notice: Subject to any disclaimer, the term of this patent is extended or adjusted under 35 U.S.C. 154(b) by 0 days. days.

(21) Appl. No.: 14/737,032

(22) Filed: Jun. 11, 2015

(65) Prior Publication Data
US 2015/0359680 A1 Dec. 17, 2015

Related U.S. Application Data

(60) Provisional application No. 62/012,509, filed on Jun. 16, 2014.

(51) Int. Cl.
*A61F 9/06* (2006.01)
*A42B 3/28* (2006.01)

(52) U.S. Cl.
CPC .............. *A61F 9/068* (2013.01); *A42B 3/283* (2013.01)

(58) Field of Classification Search
CPC ........... A42B 3/283; A42B 3/28; A42B 3/281; A42B 3/286; A61F 9/068;
(Continued)

(56) References Cited

U.S. PATENT DOCUMENTS 716,505 A 12/1902 Williams
716,506 A 12/1902 Williams
(Continued)

FOREIGN PATENT DOCUMENTS

EP 0269551 A2 6/1988
EP 0269589 A1 6/1988
(Continued)

OTHER PUBLICATIONS

Inyopools.com, How to set up the zodiac T5 suction cleaner through your skimmer, https://webarchive.org/web/20130627095500/http://www.inyopools.com/HowToPage/How-to-set-up-the-zodiac0t5-cleaner-through-your-skimmer.aspx, Jun. 27, 2013, Retreived via Wayback Machine on Apr. 19, 2016.*
(Continued)

*Primary Examiner* — Jameson Collier
*Assistant Examiner* — Heather Mangine
(74) *Attorney, Agent, or Firm* — Klintworth & Rozenblat IP LLP

(57) ABSTRACT

In one aspect, a protective headwear is provided and includes an outer shell, a first shell duct coupled to the outer shell and including a first exhaust port, and a second shell duct coupled to the outer shell and spaced apart from the first shell duct. The second shell duct includes a second exhaust port. The protective headwear also includes a manifold positioned externally of the outer shell and configured to divert airflow into at least a first potion of airflow and a second portion of airflow. The manifold includes a first diversion member coupled to and in fluid communication with the first shell duct to provide the first portion of airflow to the first shell duct, and a second diversion member coupled to and in fluid communication with the second shell duct to provide the second portion of airflow to the second shell duct.

18 Claims, 7 Drawing Sheets

(58) Field of Classification Search
CPC ... Y10T 403/7045; A43B 3/285; A43B 3/288; A43B 3/00; A43B 3/04
USPC ...... 2/8.2, 8.6, 436, 437, 410, 424, 9, 171.3; 128/201.24
See application file for complete search history.

(56) References Cited

U.S. PATENT DOCUMENTS

| | | |
|---|---|---|
| 1,182,367 A | 5/1916 | Gravell |
| 1,338,022 A | 4/1920 | Lamoreaux |
| 1,601,830 A | 10/1926 | Huntsman |
| 1,994,103 A | 3/1935 | Huey |
| 2,085,249 A | 6/1937 | Bullard |
| 2,169,745 A | 8/1939 | Shipman |
| 2,194,492 A | 3/1940 | Bowers |
| 2,411,831 A | 11/1946 | Lehmberg et al. |
| 2,487,848 A | 11/1949 | Bowers |
| 2,658,200 A | 11/1953 | Bowers, Sr. |
| 2,700,158 A | 1/1955 | Larsen |
| 2,763,006 A | 9/1956 | Amundsen |
| 3,074,072 A | 1/1963 | Edwards et al. |
| 3,214,768 A | 11/1965 | Bohner |
| 3,390,514 A | 7/1968 | Raschke |
| 3,413,972 A | 12/1968 | Depping |
| 3,430,263 A | 3/1969 | Newcomb |
| 3,609,765 A | 10/1971 | Molitoris |
| 3,629,868 A | 12/1971 | Greenlee |
| 3,668,362 A | 6/1972 | Kirchner |
| 3,685,512 A | 8/1972 | Raschke |
| 3,696,442 A | 10/1972 | Amundsen |
| 3,724,740 A | 4/1973 | Imamura et al. |
| 3,868,727 A | 3/1975 | Paschall |
| 3,881,478 A * | 5/1975 | Rosendahl ............ A42B 3/0406 128/200.28 |
| 3,914,796 A | 10/1975 | Barta |
| 3,927,668 A | 12/1975 | Raschke |
| 3,943,573 A | 3/1976 | Budmiger |
| 3,955,570 A * | 5/1976 | Hutter, III .......... A41D 13/1153 128/201.23 |
| 4,011,865 A | 3/1977 | Morishita |
| 4,031,564 A | 6/1977 | Wood |
| 4,040,123 A | 8/1977 | Williams |
| 4,052,984 A | 10/1977 | Brockway |
| 4,080,664 A | 3/1978 | Morris |
| 4,109,320 A | 8/1978 | Anderson |
| 4,149,908 A | 4/1979 | Thall et al. |
| 4,172,294 A | 10/1979 | Harris |
| 4,185,329 A | 1/1980 | Sarazen |
| 4,236,514 A | 12/1980 | Moretti |
| 4,271,833 A | 6/1981 | Moretti |
| 4,293,757 A | 10/1981 | Niemi |
| 4,309,774 A | 1/1982 | Guzowski |
| D270,642 S | 9/1983 | Watts |
| 4,452,240 A | 6/1984 | Moretti |
| 4,455,683 A | 6/1984 | Moretti |
| 4,464,800 A | 8/1984 | Edwards |
| 4,479,738 A | 10/1984 | Kubnick |
| 4,484,575 A | 11/1984 | Brockway et al. |
| 4,499,630 A | 2/1985 | Harris |
| 4,513,452 A | 4/1985 | Rankin, Sr. |
| 4,542,538 A | 9/1985 | Moretti et al. |
| 4,556,991 A | 12/1985 | Margaronis |
| 4,561,162 A | 12/1985 | Brockway et al. |
| 4,576,669 A | 3/1986 | Caputo |
| 4,619,254 A | 10/1986 | Moretti et al. |
| 4,649,571 A | 3/1987 | Falkiner |
| 4,672,968 A | 6/1987 | Lenox et al. |
| 4,694,141 A | 9/1987 | Hahn |
| 4,697,058 A | 9/1987 | Mueller |
| 4,721,517 A | 1/1988 | Cloutier |
| 4,726,104 A | 2/1988 | Foster et al. |
| 4,793,001 A | 12/1988 | Accardi |
| 4,853,973 A | 8/1989 | Boochard |
| 4,867,770 A | 9/1989 | Feeney |
| 4,875,235 A | 10/1989 | Kuhlman |
| 4,883,547 A | 11/1989 | Japuntich |
| 4,890,335 A | 1/1990 | Crowson |
| 4,899,740 A | 2/1990 | Napolitano |
| 4,937,879 A | 7/1990 | Hall |
| 4,988,342 A | 1/1991 | Herweck et al. |
| 4,989,598 A | 2/1991 | Berg et al. |
| D316,020 S | 4/1991 | Fushiya |
| 5,003,632 A | 4/1991 | Claude |
| 5,012,528 A | 5/1991 | Pernicka |
| 5,029,342 A | 7/1991 | Stein et al. |
| 5,031,237 A | 7/1991 | Honrud |
| 5,040,528 A | 8/1991 | O'Neill |
| 5,044,019 A | 9/1991 | Shewchenko |
| 5,077,836 A | 1/1992 | Idoff et al. |
| 5,088,115 A | 2/1992 | Napolitano |
| 5,123,114 A | 6/1992 | Desanti |
| D329,590 S | 9/1992 | Chapman |
| 5,154,712 A | 10/1992 | Herweck et al. |
| 5,189,735 A | 3/1993 | Corona |
| 5,191,468 A | 3/1993 | Mases |
| 5,351,151 A | 9/1994 | Levy |
| 5,357,951 A | 10/1994 | Ratner |
| 5,386,592 A | 2/1995 | Checkeroski |
| 5,412,811 A | 5/1995 | Hildenbrand |
| 5,464,010 A | 11/1995 | Byram |
| D365,666 S | 12/1995 | Gumpp |
| 5,549,104 A | 8/1996 | Bullard |
| 5,555,879 A | 9/1996 | Helin |
| 5,561,855 A | 10/1996 | Mcfall |
| 5,645,056 A | 7/1997 | Pomeroy |
| 5,724,119 A | 3/1998 | Leight |
| D393,933 S | 4/1998 | Huh |
| 5,749,096 A | 5/1998 | Fergason et al. |
| 5,752,280 A | 5/1998 | Hill |
| D398,421 S | 9/1998 | Crafoord |
| 5,896,579 A | 4/1999 | Johnson |
| 5,924,420 A | 7/1999 | Reischel et al. |
| 5,954,055 A | 9/1999 | Miyake |
| 5,991,072 A | 11/1999 | Solyntjes et al. |
| 6,012,452 A | 1/2000 | Pagan |
| D421,116 S | 2/2000 | Mattila |
| 6,032,297 A | 3/2000 | Barthold et al. |
| 6,035,451 A | 3/2000 | Burns et al. |
| 6,055,983 A | 5/2000 | Metzger |
| 6,070,579 A | 6/2000 | Bryant et al. |
| 6,119,692 A | 9/2000 | Byram |
| D433,751 S | 11/2000 | Reischel |
| 6,148,817 A | 11/2000 | Bryant et al. |
| 6,154,881 A | 12/2000 | Lee |
| 6,185,739 B1 | 2/2001 | Verkic et al. |
| 6,260,197 B1 | 7/2001 | Hoogewind |
| 6,260,917 B1 | 7/2001 | Marechal |
| 6,264,392 B1 | 7/2001 | Wise |
| 6,290,642 B1 | 9/2001 | Reinhard et al. |
| D449,103 S | 10/2001 | Legare |
| 6,298,498 B1 | 10/2001 | Burns et al. |
| 6,325,754 B1 | 12/2001 | Reinhard et al. |
| 6,341,382 B1 | 1/2002 | Ryvin et al. |
| 6,367,085 B1 | 4/2002 | Berg |
| 6,370,748 B1 | 4/2002 | Baccini |
| 6,393,617 B1 | 5/2002 | Paris |
| 6,465,102 B1 | 10/2002 | Honigfort et al. |
| D465,568 S | 11/2002 | Petherbridge |
| D467,489 S | 12/2002 | Rubinson |
| 6,591,837 B1 | 7/2003 | Byram |
| 6,598,236 B1 | 7/2003 | Gantt |
| 6,609,516 B2 | 8/2003 | Hollander et al. |
| 6,637,091 B2 | 10/2003 | Halstead et al. |
| 6,715,489 B2 | 4/2004 | Bostock et al. |
| 6,715,490 B2 | 4/2004 | Byram |
| D489,492 S | 5/2004 | Wu |
| D492,559 S | 7/2004 | Itano |
| 6,763,830 B1 | 7/2004 | Davis et al. |
| 6,782,558 B1 | 8/2004 | Keen, Sr. et al. |
| 6,902,774 B2 | 6/2005 | Nicolussi |
| 6,911,108 B2 | 6/2005 | Sarmiento |
| 6,973,676 B1 * | 12/2005 | Simpson ................ A42B 3/288 128/201.24 |
| 7,000,262 B2 | 2/2006 | Bielefeld |

(56) References Cited

U.S. PATENT DOCUMENTS

| | | |
|---|---|---|
| D520,856 S | 5/2006 | Osiecki |
| D520,859 S | 5/2006 | Osiecki |
| D521,190 S | 5/2006 | Wu |
| 7,043,772 B2 | 5/2006 | Bullard |
| 7,069,930 B2 | 7/2006 | Bostock et al. |
| 7,089,603 B2 | 8/2006 | Ketterer et al. |
| 7,093,302 B1 | 8/2006 | Burns |
| D530,185 S | 10/2006 | Osiecki |
| 7,120,939 B1 | 10/2006 | Howard |
| 7,150,047 B2 | 12/2006 | Fergason |
| 7,156,093 B2 | 1/2007 | Bullard |
| 7,178,932 B1 | 2/2007 | Buckman |
| 7,188,622 B2 | 3/2007 | Martin et al. |
| 7,213,271 B1 | 5/2007 | Bielefeld |
| D543,828 S | 6/2007 | Strutin-Belinoff |
| D557,128 S | 12/2007 | Sawdon |
| 7,358,458 B2 | 4/2008 | Daniel |
| 7,393,712 B2 | 7/2008 | Smith et al. |
| 7,410,095 B2 | 8/2008 | Selover |
| 7,441,282 B2 | 10/2008 | Heine |
| 7,454,800 B2 | 11/2008 | Taylor et al. |
| D584,003 S | 12/2008 | Juhlin |
| 7,493,900 B1 | 2/2009 | Japuntich et al. |
| D589,654 S | 3/2009 | Juhlin |
| D589,776 S | 4/2009 | Camp |
| D590,232 S | 4/2009 | Demers |
| 7,534,005 B1 | 5/2009 | Buckman |
| D600,094 S | 9/2009 | Hwang |
| D602,639 S | 10/2009 | Ho |
| 7,644,478 B2 | 1/2010 | Boyer |
| 7,699,053 B1 | 4/2010 | Bullard |
| 7,718,031 B2 | 5/2010 | Kang et al. |
| D617,459 S | 6/2010 | Bogue |
| D626,963 S | 11/2010 | Kim |
| D632,944 S | 2/2011 | Kang |
| D635,721 S | 4/2011 | Cheng |
| 7,971,267 B2 | 7/2011 | Huh |
| 8,015,970 B2 | 9/2011 | Klun et al. |
| 8,056,152 B2 | 11/2011 | Brace |
| 8,087,254 B2 | 1/2012 | Arnold |
| 8,104,094 B2 | 1/2012 | Uttrachi |
| D654,224 S | 2/2012 | Wu |
| D654,634 S | 2/2012 | Wu |
| 8,171,933 B2 | 5/2012 | Xue et al. |
| 8,214,920 B1 | 7/2012 | Edgar |
| D667,173 S | 9/2012 | Juhlin et al. |
| 8,286,269 B2 | 10/2012 | Springer et al. |
| 8,286,634 B2 | 10/2012 | Madaus et al. |
| 8,336,113 B2 | 12/2012 | Uttrachi |
| 8,336,114 B1 | 12/2012 | Lee |
| D674,150 S | 1/2013 | Juhlin et al. |
| D674,153 S | 1/2013 | Daniels et al. |
| 8,359,662 B2 | 1/2013 | Viljanen |
| D676,551 S | 2/2013 | Desai |
| 8,365,732 B2 | 2/2013 | Johnstone |
| 8,381,312 B2 | 2/2013 | Seo |
| 8,387,162 B2 | 3/2013 | Huh |
| D684,252 S | 6/2013 | Okada |
| 8,528,560 B2 | 9/2013 | Duffy |
| 8,551,279 B2 | 10/2013 | Johnson et al. |
| 8,584,265 B2 | 11/2013 | Lilenthal et al. |
| 8,627,517 B2 | 1/2014 | Ahlgren et al. |
| 8,640,704 B2 | 2/2014 | Spoo et al. |
| 8,661,570 B2 | 3/2014 | Huh |
| 8,679,853 B2 | 3/2014 | Bhullar et al. |
| 8,684,004 B2 | 4/2014 | Eifler |
| D710,546 S | 8/2014 | Wu |
| 8,826,464 B2 | 9/2014 | Wu |
| 8,932,424 B2 | 1/2015 | Johnson et al. |
| D722,259 S | 2/2015 | Conner |
| 8,990,963 B2 | 3/2015 | Matthews |
| D735,949 S | 8/2015 | Dion |
| D735,951 S | 8/2015 | Birath et al. |
| 9,125,448 B2 | 9/2015 | Klotz |
| 9,155,923 B2 | 10/2015 | Proctor |
| D742,596 S | 11/2015 | Peng |
| D743,629 S | 11/2015 | Peng |
| D747,556 S | 1/2016 | Fujita |
| D749,796 S | 2/2016 | Barmore |
| 9,427,040 B2 | 8/2016 | Leyland |
| D767,829 S | 9/2016 | Wu |
| 9,516,911 B2 | 12/2016 | Happel |
| 2003/0135911 A1 | 7/2003 | Wang-Lee |
| 2004/0179149 A1 | 9/2004 | Wang-Lee |
| 2004/0262364 A1 | 12/2004 | Halstead et al. |
| 2005/0012197 A1 | 1/2005 | Smith et al. |
| 2005/0017641 A1 | 1/2005 | Kruger et al. |
| 2005/0268907 A1 | 12/2005 | McFarlane |
| 2006/0010551 A1 | 1/2006 | Bishop et al. |
| 2006/0080761 A1 | 4/2006 | Huh |
| 2006/0101552 A1 | 5/2006 | Lee et al. |
| 2006/0107431 A1 | 5/2006 | Curran et al. |
| 2006/0201513 A1 | 9/2006 | Chu |
| 2006/0225187 A1 | 10/2006 | Wu |
| 2006/0231100 A1 | 10/2006 | Walker et al. |
| 2007/0050892 A1 | 3/2007 | Charles |
| 2007/0068529 A1 | 3/2007 | Kalatoor et al. |
| 2007/0088234 A1 | 4/2007 | Tseng |
| 2007/0089215 A1 | 4/2007 | Biche et al. |
| 2007/0113318 A1* | 5/2007 | Weston ............... A42B 3/281 |
| | | 2/171.3 |
| 2007/0215254 A1 | 9/2007 | Birke et al. |
| 2007/0220649 A1 | 9/2007 | Huh |
| 2007/0226881 A1 | 10/2007 | Reinhard et al. |
| 2007/0245467 A1 | 10/2007 | Lilenthal |
| 2008/0011303 A1 | 1/2008 | Angadjivand et al. |
| 2008/0060102 A1 | 3/2008 | Matthews |
| 2008/0095898 A1 | 4/2008 | Mansuino |
| 2008/0106001 A1 | 5/2008 | Slafer |
| 2008/0189820 A1 | 8/2008 | Duffy et al. |
| 2009/0031485 A1 | 2/2009 | Prusinski |
| 2009/0044808 A1 | 2/2009 | Guney et al. |
| 2009/0055987 A1 | 3/2009 | Becker et al. |
| 2009/0089908 A1* | 4/2009 | Huh ................. A62B 18/003 |
| | | 2/8.6 |
| 2009/0184099 A1 | 7/2009 | Eddington et al. |
| 2009/0210988 A1 | 8/2009 | Becker et al. |
| 2009/0210989 A1 | 8/2009 | Becker et al. |
| 2009/0277451 A1 | 11/2009 | Weinberg |
| 2009/0277462 A1 | 11/2009 | Garber et al. |
| 2009/0277814 A1 | 11/2009 | Hamerly et al. |
| 2009/0283096 A1 | 11/2009 | Cerbini |
| 2009/0298024 A1 | 12/2009 | Batzler |
| 2010/0050325 A1 | 3/2010 | Wang-Lee |
| 2010/0154805 A1 | 6/2010 | Duffy et al. |
| 2010/0229274 A1 | 9/2010 | Ahlgren |
| 2010/0229286 A1 | 9/2010 | Ahlgren |
| 2010/0235971 A1 | 9/2010 | Ahlgren |
| 2010/0294270 A1* | 11/2010 | Curran ............... A42B 3/286 |
| | | 128/201.23 |
| 2011/0101890 A1 | 5/2011 | Robinson |
| 2011/0167542 A1 | 7/2011 | Bayne |
| 2011/0179541 A1 | 7/2011 | Wright |
| 2011/0219506 A1 | 9/2011 | Uttrachi |
| 2011/0226256 A1 | 9/2011 | Dubach |
| 2011/0265790 A1* | 11/2011 | Walker ............... A62B 9/04 |
| | | 128/201.23 |
| 2011/0266718 A1 | 11/2011 | Angadjivand et al. |
| 2012/0024289 A1 | 2/2012 | Johnstone et al. |
| 2012/0144565 A1 | 6/2012 | Huh |
| 2012/0157904 A1 | 6/2012 | Stein |
| 2012/0184046 A1 | 7/2012 | Atkin |
| 2012/0260920 A1 | 10/2012 | Choi et al. |
| 2012/0286958 A1 | 11/2012 | Dunbar |
| 2013/0111648 A1 | 5/2013 | Huh |
| 2013/0152919 A1 | 6/2013 | Billingsley et al. |
| 2013/0220332 A1 | 8/2013 | Baska |
| 2013/0291876 A1 | 11/2013 | Angadjivand et al. |
| 2013/0305524 A1 | 11/2013 | Hohenthanner et al. |
| 2013/0312151 A1 | 11/2013 | North |
| 2014/0007881 A1 | 1/2014 | Rummery et al. |
| 2014/0026897 A1 | 1/2014 | Saroch et al. |
| 2014/0110685 A1 | 4/2014 | Hong et al. |
| 2014/0166001 A1 | 6/2014 | Kooken |

(56) References Cited

U.S. PATENT DOCUMENTS

| | | |
|---|---|---|
| 2014/0168546 A1 | 6/2014 | Magnusson et al. |
| 2014/0182600 A1 | 7/2014 | Duffy |
| 2014/0190486 A1 | 7/2014 | Dunn et al. |
| 2014/0224256 A1 | 8/2014 | Skov et al. |
| 2014/0260933 A1 | 9/2014 | Ardiff et al. |
| 2014/0298557 A1 | 10/2014 | Townsend, Jr. |
| 2014/0332005 A1 | 11/2014 | Kunz et al. |
| 2015/0059771 A1 | 3/2015 | Duffy |
| 2015/0069036 A1 | 3/2015 | Farah |
| 2015/0143669 A1 | 5/2015 | Pereira et al. |
| 2016/0081856 A1 | 3/2016 | Hofer-Kraner |
| 2016/0360821 A1 | 12/2016 | Benton |

FOREIGN PATENT DOCUMENTS

| | | |
|---|---|---|
| EP | 0309633 A1 | 4/1989 |
| EP | 0417026 A1 | 3/1991 |
| EP | 0582286 A1 | 2/1994 |
| EP | 0894443 A2 | 2/1999 |
| EP | 0911049 A1 | 4/1999 |
| EP | 0983190 A1 | 3/2000 |
| EP | 0983192 B1 | 3/2000 |
| EP | 1041865 A2 | 10/2000 |
| EP | 1061824 A1 | 12/2000 |
| EP | 1114871 A1 | 7/2001 |
| EP | 1506034 A2 | 2/2005 |
| EP | 1516645 A2 | 3/2005 |
| EP | 1699531 A1 | 9/2006 |
| EP | 1773148 A1 | 4/2007 |
| EP | 1800706 A1 | 6/2007 |
| EP | 1809386 A1 | 7/2007 |
| EP | 1847298 A1 | 10/2007 |
| EP | 1898735 A1 | 3/2008 |
| EP | 1951123 A1 | 8/2008 |
| EP | 2099532 A1 | 9/2009 |
| EP | 2 184 039 A1 | 5/2010 |
| EP | 2298096 A2 | 3/2011 |
| EP | 2298419 A1 | 3/2011 |
| EP | 2314353 A1 | 4/2011 |
| EP | 2349426 A1 | 8/2011 |
| EP | 2 462 825 A2 | 6/2012 |
| EP | 2 462 826 A2 | 6/2012 |
| EP | 2477588 A1 | 7/2012 |
| EP | 2486815 A1 | 8/2012 |
| EP | 2589308 A1 | 5/2013 |
| EP | 2589309 A1 | 5/2013 |
| EP | 2630993 A1 | 8/2013 |
| WO | 1984/003193 | 8/1984 |
| WO | 1986/003128 | 6/1986 |
| WO | 1989/000919 A1 | 2/1989 |
| WO | 1993/003636 A1 | 3/1993 |
| WO | 1993/018726 A1 | 9/1993 |
| WO | 1994/023680 A1 | 10/1994 |
| WO | 1995/025005 A1 | 9/1995 |
| WO | 1996/028217 A1 | 9/1996 |
| WO | 1998/006244 A1 | 2/1998 |
| WO | 1999/016508 A1 | 4/1999 |
| WO | 1999/045810 | 9/1999 |
| WO | 2000/003899 A2 | 1/2000 |
| WO | 2001/078839 A2 | 10/2001 |
| WO | 2002/002191 A1 | 1/2002 |
| WO | 2003/020438 A2 | 3/2003 |
| WO | 2003/068319 A1 | 8/2003 |
| WO | 2003/097145 A2 | 11/2003 |
| WO | 2003/097968 A1 | 11/2003 |
| WO | 2003/103425 A1 | 12/2003 |
| WO | 2004/035142 A1 | 4/2004 |
| WO | 2004/091726 A1 | 10/2004 |
| WO | 2004/106082 A1 | 12/2004 |
| WO | 2005/000411 A1 | 1/2005 |
| WO | 2005/002481 A1 | 1/2005 |
| WO | 2005/008275 A1 | 1/2005 |
| WO | 2005/065780 A1 | 7/2005 |
| WO | 2006/019472 A1 | 2/2006 |
| WO | 2006/026690 A2 | 3/2006 |
| WO | 2006026690 A2 | 3/2006 |
| WO | 2006/043028 A1 | 4/2006 |
| WO | 2006/055114 A1 | 5/2006 |
| WO | 2006/055151 A1 | 5/2006 |
| WO | 2006/055152 A1 | 5/2006 |
| WO | 2006/086618 A1 | 8/2006 |
| WO | 2007/024865 | 3/2007 |
| WO | 2007/038202 A1 | 4/2007 |
| WO | 2007/045008 A1 | 4/2007 |
| WO | 2007/071429 | 6/2007 |
| WO | 2007/100849 A2 | 9/2007 |
| WO | 2007/135700 A2 | 11/2007 |
| WO | 2008/025083 A1 | 3/2008 |
| WO | 2008/081489 A1 | 7/2008 |
| WO | 2008/085546 A2 | 7/2008 |
| WO | 2008/145175 A1 | 12/2008 |
| WO | 2009/003057 A1 | 12/2008 |
| WO | 2009/003691 A1 | 1/2009 |
| WO | 2009/014798 A1 | 1/2009 |
| WO | 2009/032823 A1 | 3/2009 |
| WO | 2009/048829 A1 | 4/2009 |
| WO | 2009/048836 A1 | 4/2009 |
| WO | 2009/078043 A1 | 6/2009 |
| WO | 2009/091785 A1 | 7/2009 |
| WO | 2009/146359 A1 | 12/2009 |
| WO | 2010/023370 A1 | 3/2010 |
| WO | 2010/031126 A1 | 3/2010 |
| WO | 2010/043966 A2 | 4/2010 |
| WO | 2010/075397 A2 | 7/2010 |
| WO | 2010/080201 A1 | 7/2010 |
| WO | 2011/038458 A1 | 4/2011 |
| WO | 2011/133207 A2 | 10/2011 |
| WO | 2012/024728 A1 | 3/2012 |
| WO | 2012/089963 A1 | 7/2012 |
| WO | 2012/097762 A1 | 7/2012 |
| WO | 2012/110514 A1 | 8/2012 |
| WO | 2012/146883 A1 | 11/2012 |
| WO | 2013/026092 A1 | 2/2013 |
| WO | 2013/053082 A1 | 4/2013 |
| WO | 2013/075166 A1 | 5/2013 |
| WO | 2013/117926 A1 | 8/2013 |
| WO | 2013/169467 A1 | 11/2013 |
| WO | 2014/015382 A1 | 1/2014 |
| WO | 2014/091293 A1 | 6/2014 |
| WO | 2014/092989 A1 | 6/2014 |
| WO | 2014/105475 A1 | 7/2014 |
| WO | 2014/110626 A1 | 7/2014 |
| WO | 2014/165906 A1 | 10/2014 |
| WO | WO 2014160149 A2 * | 10/2014 ............ A42B 3/286 |
| WO | 2014/197022 A2 | 12/2014 |
| WO | 2015/010170 A1 | 1/2015 |
| WO | 2015/031141 A2 | 3/2015 |
| WO | 2015/036652 A1 | 3/2015 |

OTHER PUBLICATIONS

International Search Report and Written Opinion for PCT/US2015/033054 dated Aug. 31, 2015, 12 pages.
International Search Report and Written Opinion for PCT/US2015/035714 dated Oct. 8, 2015, 11 pages.
International Search Report and Written Opinion for PCT/US2015/035713 dated Oct. 27, 2015, 17 pages.
International Search Report and Written Opinion for PCT/US2015/065213 dated Mar. 16, 2016, 13 pages.
Miller 9400i welding helmet with an integrated grind shield, published at least as early as Jun. 16, 2014, 1 page.
Speedglas 9100FX welding helmet with an integrated grind shield, published at least as early as Jun. 16, 2014, 1 page.
Speedglas 9002X Flexview welding helmet with an integrated grind shield, published at least as early as Jun. 16, 2014, 1 page.
Miller 9400i PAPR welding helmet with powered air purifying system, belt mounted blower with breathing tube connecting to manifold inside head assembly, published at least as early as Jun. 16, 2014, 1 page.
Speedglas 9100X Air Adflo welding helmet with airflow delivery mechanism, published at least as early as Jun. 16, 2014, 1 page.

(56) References Cited

OTHER PUBLICATIONS

Speedglas 9100FX Air Adflo welding helmet with airflow delivery mechanism, published at least as early as Jun. 16, 2014, 1 page.
Miller headgear for a welding helmet, published at least as early as Jun. 16, 2014, 1 page.
Speedglas headgear for a welding helmet, published at least as early as Jun. 16, 2014, 1 page.

* cited by examiner

PROTECTIVE HEADWEAR WITH AIRFLOW

RELATED APPLICATIONS

The present application claims the priority benefit of U.S. Provisional Patent Application Ser. No. 62/012,509, filed Jun. 16, 2014, the content of which is incorporated by reference herein.

FIELD OF THE INVENTION

The present disclosure generally relates to protective headwear and, more particularly, to protective headwear with airflow.

BACKGROUND

Protective headwear such as, for example, welding helmets may be used in environments requiring respirators or other manners of introducing air into an interior of the protective headwear such as, for example, a powered air purifying respirator (PAPR) or a supplied air respirator (SAR). Some of these conventional welding helmets include a blower unit that delivers air to a manifold, which distributes air to an interior space of the welding helmet. Such conventional welding helmets lack comfort because they are heavy and distribute air to undesirable locations within the welding helmet. Some conventional welding helmets include a manifold or hose that extends over a wearer's head and distributes the air downward over a front of the wearer's face and into the wearer's eyes. Such a manifold or hose is heavy in construction and positions a lot of weight above and in front of a wearer's head and face to provide a center of gravity above and in front of a wearer's head and face. A center of gravity in this position applies significant torque and stress on a wearer's head, neck and body.

While the primary purpose of protective headwear with airflow is to provide respiratory protection, it also serves to protect users from heat stress. The poor design of the airflow delivery system does not maximize its potential for assisting in the body's thermoregulation to minimize heat stress. Additionally the poor design of protective headwear with airflow leads to inefficient use of the airflow to maximize the user's thermal comfort and perception of air circulation which play a key role in defining user comfort. The comfort of protective headwear with airflow may have an impact on productivity and quality of the welder. Additionally, the air of conventional protective headwear is blown directly over and/or into the wearer's eyes, thereby drying the wearer's eyes or otherwise making the wearer uncomfortable.

SUMMARY

It is therefore desirable to have protective headwear that has an appropriate weight and location of a center of gravity, and provides airflow to an appropriate location within an interior of the protective headwear to effectively cool.

In one aspect, a protective headwear for providing airflow to an interior thereof is provided.

In one aspect, a protective headwear is provided and includes an airflow device for providing airflow to an interior of the protective headwear.

In one aspect, a protective headwear is provided and includes an outer shell including a first helmet duct and a second helmet duct spaced apart from the first helmet duct. Each of the first and second helmet ducts includes an exhaust port. The protective headwear also includes an airflow device in fluid communication with the outer shell. The airflow device includes an air source for providing an airflow and a coupling member coupled to the outer shell. The coupling member includes a first duct coupled to and in fluid communication with the first helmet duct to provide a first portion of the airflow to the first helmet duct, and a second duct coupled to and in fluid communication with the second helmet duct to provide a second portion of the airflow to the second helmet duct. The protective headwear may be a welding helmet.

In one aspect, a protective headwear is provided and includes an outer shell, a first shell duct coupled to the outer shell and including a first exhaust port, and a second shell duct coupled to the outer shell and spaced apart from the first shell duct. The second shell duct includes a second exhaust port. The protective headwear also includes a manifold positioned externally of the outer shell and configured to divert airflow into at least a first potion of airflow and a second portion of airflow. The manifold includes a first diversion member coupled to and in fluid communication with the first shell duct to provide the first portion of airflow to the first shell duct, and a second diversion member coupled to and in fluid communication with the second shell duct to provide the second portion of airflow to the second shell duct.

In one aspect, the first exhaust port of the first shell duct may be one of a plurality of exhaust ports, and the second exhaust port of the second shell duct may be one of a plurality of exhaust ports.

In one aspect, one of the plurality of exhaust ports of the first shell duct may be positioned in a top half of the outer shell and another one of the plurality of exhaust ports of the first shell duct may be positioned in a bottom half of the outer shell, and one of the plurality of exhaust ports of the second shell duct may be positioned in a top half of the outer shell and another one of the plurality of exhaust ports of the second shell duct may be positioned in a bottom half of the outer shell.

In one aspect, at least one of the plurality of exhaust ports of the first shell duct may be adjustable to adjust at least one of airflow direction and airflow volume exhaustible from the at least one of the plurality of exhaust ports of the first shell duct, and at least one of the plurality of exhaust ports of the second shell duct may be adjustable to adjust at least one of airflow direction and airflow volume exhaustible from the at least one of the plurality of exhaust ports of the second shell duct.

In one aspect, the at least one of the plurality of exhaust ports of the first shell duct that is adjustable may be rotatable to adjust air flow direction and may include a damper for adjusting airflow volume exhaustible there from, and the at least one of the plurality of exhaust ports of the second shell duct that is adjustable may be rotatable to adjust air flow direction and may include a damper for adjusting airflow volume exhaustible there from.

In one aspect, the at least one of the plurality of exhaust ports of the first shell duct that is adjustable may adjust both airflow direction and airflow volume exhaustible there from, and the at least one of the plurality of exhaust ports of the second shell duct that is adjustable may adjust both airflow direction and airflow volume exhaustible there from.

In one aspect, at least two of the plurality of exhaust ports of the first shell duct may be adjustable to adjust at least one of airflow direction and airflow volume exhaustible there from, and at least two of the plurality of exhaust ports of the second shell duct may be adjustable to adjust at least one of airflow direction and airflow volume exhaustible there from.

In one aspect, one of the plurality of exhaust ports of the first shell duct may be configured to exhaust air onto a wearer's forehead and another of the plurality of exhaust ports of the first shell duct may be configured to exhaust air onto a wearer's chin, and one of the plurality of exhaust ports of the second shell duct may be configured to exhaust air onto a wearer's forehead and another of the plurality of exhaust ports of the second shell duct may be configured to exhaust air onto a wearer's chin.

In one aspect, the first exhaust port may be positioned in a bottom half of the outer shell, and the second exhaust port may be positioned in the bottom half of the outer shell.

In one aspect, the protective headwear may be a welding helmet.

In one aspect, the protective headwear may further include a first flexible duct coupled to and between the first shell duct and the first diversion member to provide the first portion of airflow from the first diversion member to the first shell duct, and a second flexible duct coupled to and between the second shell duct and the second diversion member to provide the second portion of airflow from the second diversion member to the second shell duct.

In one aspect, one of a first end of the first flexible duct and an end of the first diversion member may include a projection and the other one of the first end of the first flexible duct and the end of the first diversion member may include an aperture. The projection may be at least partially received in the aperture to couple the first flexible duct to the first diversion member. One of a second end of the first flexible duct and an end of the first shell duct may include a projection and the other one of the second end of the first flexible duct and the end of the first shell duct may include an aperture. The projection may be at least partially received in the aperture to couple the first flexible duct to the first shell duct.

In one aspect, the first shell duct may be offset to a first side of a plane extending through a center of the outer shell from a front to a rear of the outer shell, and the second shell duct may be offset to a second side of the plane.

In one aspect, a protective headwear is provided and includes an outer shell including an interior surface. The interior surface has a first side, a second side opposite the first side, a front between the first and second sides, and a top between the first and second sides. The protective headwear also includes a duct at least partially coupled to and extending along the first side of the interior surface of the outer shell. The duct includes an inlet through which air is configured to be introduced into the duct and an exhaust port through which air is configured to be exhausted from the duct and into an interior of the outer shell. The exhaust port may be positioned along the first side of the interior surface.

In one aspect, the exhaust port may be positioned in a bottom half of the outer shell.

In one aspect, the inlet may be positioned in a top half of the outer shell.

In one aspect, the exhaust port is a first exhaust port, the duct may further include a second exhaust port. The first exhaust port may be positioned in a bottom half of the outer shell and the second exhaust port may be positioned in a top half of the outer shell.

In one aspect, the exhaust port may be adjustable to adjust at least one of airflow direction and airflow volume exhaustible there from.

In one aspect, the exhaust port may be adjustable to adjust airflow direction and airflow volume exhaustible there from.

In one aspect, the duct is a first duct, the inlet is a first inlet and the exhaust port is a first exhaust port. The protective headwear may further include a second duct at least partially coupled to and extending along the second side of the interior surface of the outer shell. The second duct may include a second inlet through which air is configured to be introduced into the second duct and a second exhaust port through which air is configured to be exhausted from the second duct and into the interior of the outer shell. The second exhaust port may be positioned along the second side of the interior surface.

In one aspect, the first exhaust port and the second exhaust port may be positioned in a bottom half of the outer shell, and the first inlet and the second inlet may be positioned in a top half of the outer shell.

In one aspect, at least a portion of air exhaustible from the exhaust port may be configured to be exhausted from the exhaust port substantially perpendicular to the first side of the interior surface.

In one aspect, at least a portion of air exhaustible from the exhaust port may be configured to be exhausted from the exhaust port away from the first side of the interior surface and toward the second side of the interior surface.

In one aspect, a protective headwear is provided and includes a headgear configured to engage a wearer's head and at least partially support the protective headwear on a wearer's head. The headgear includes a front, a rear opposite the front, a right side, and a left side opposite the right side. The protective headwear also includes an outer shell coupled to the headgear and including a shield positioned to the front of the headgear, and a duct at least partially coupled to and at least partially positioned in an interior of the outer shell. The protective headwear further includes a manifold positioned to the rear of the headgear and configured to divert airflow into at least a first potion of airflow and a second portion of airflow.

In one aspect, the manifold may include a first diversion member configured to divert the first portion of airflow and a second diversion member configured to divert the second portion of airflow. One of the first and second diversion members may be in fluid communication with the duct and may provide one of the first and second portions of airflow to the duct.

In one aspect, the protective headwear may further include a flexible duct coupled to and between the duct and the manifold to provide one of the first and second portions of airflow from the manifold to the duct.

In one aspect, the flexible duct may couple to the manifold to the rear of the headgear and may extend toward a top of the headgear.

In one aspect, the duct may be a first duct coupled to a first side of an interior surface of the outer shell and may at least partially extend along the first side. The protective headwear may further include a second duct coupled to a second side of the interior surface of the outer shell and may at least partially extend along the second side. The second side may be opposite the first side. The manifold may be coupled to and in fluid communication with both the first and second ducts to provide the first portion of airflow to the first duct and the second portion of airflow to the second duct.

In one aspect, the duct may be offset from a plane extending through a center of the headgear from the front to the rear of the headgear to one of the right or left sides of the headgear.

BRIEF DESCRIPTION OF THE DRAWINGS

The disclosure can be better understood with reference to the following drawings and description. The components in the figures are not necessarily to scale, emphasis instead being placed upon illustrating the principles of the disclosure.

DETAILED DESCRIPTION

Figure 1:
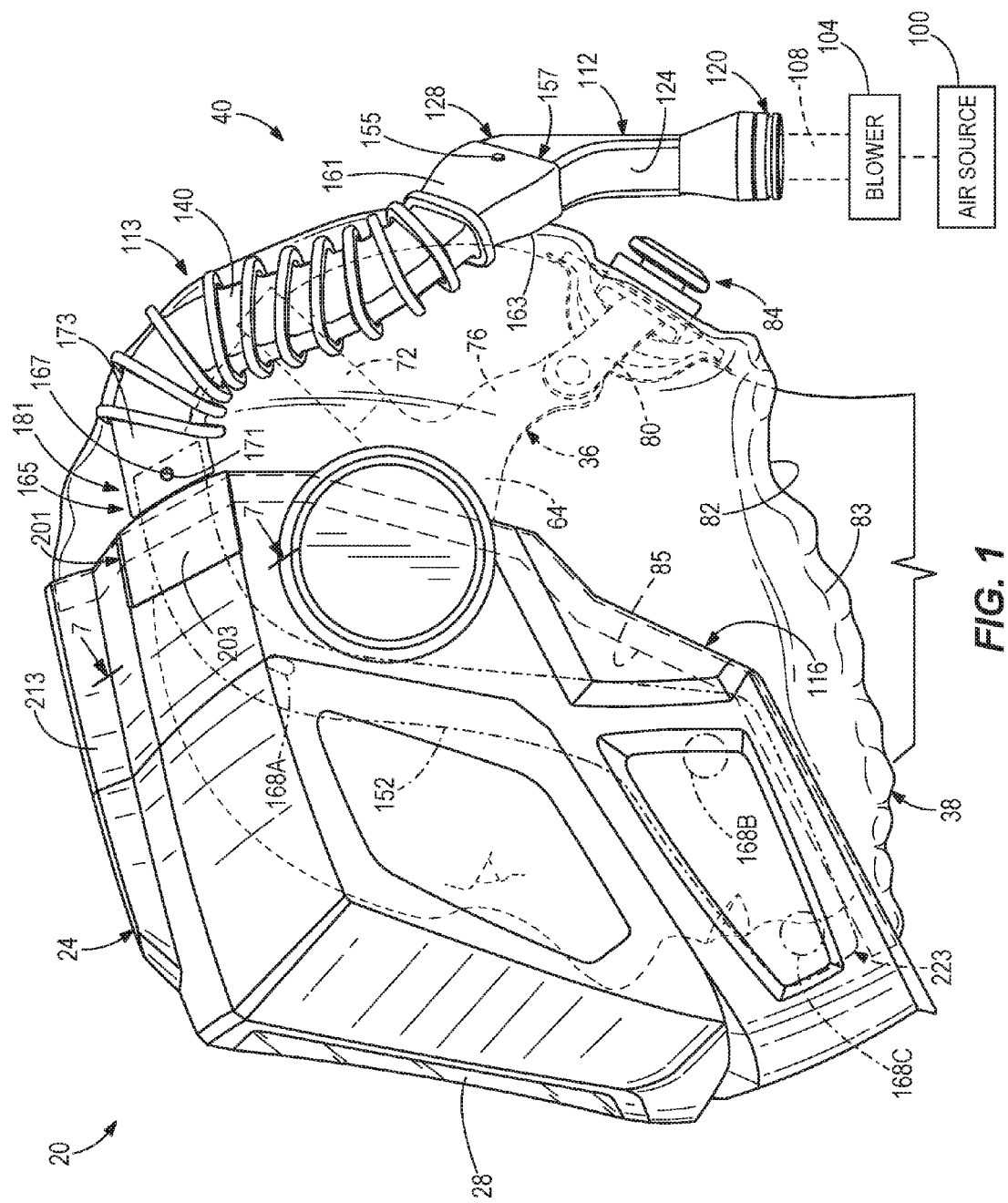
FIG. 1 is a side view of one example of protective headwear including one example of an airflow device for delivering air to an interior of the protective headwear, according to one aspect of the present disclosure.

Referring to FIGS. 1-7, one example of protective headwear 20 is illustrated. In this illustrated example, the protective headwear 20 is a welding helmet. In other examples, the protective headwear may be other types of protective headwear including, but not limited to, hard hats, bicycle helmets, military helmets, grinding shields, or any other type of headwear capable of providing protection to a wearer's head.

Returning to the illustrated example, the protective headwear 20 includes an outer shell 24, a first shield 28, a second shield 32 (beneath the first shield 28—see FIGS. 3 and 6), headgear 36 within the outer shell 24 to support the protective headwear 20 on a wearer's head, a head sleeve 38 coupled to the outer shell 24 and configured to at least partially surround a wearer's head, and an airflow device 40. The first shield 28 may be a welding shield and is coupled to the outer shell 24 over the second shield 32. The first shield 28 is darkened or capable of darkening in order to inhibit damage to a wearer's eyes while performing a welding process. In one example, the first shield 28 is an auto-darkening welding shield. The second shield 32 is coupled to the outer shell 24 beneath the first shield 28 and is darkened less than the first shield 28. In one example, the second shield 32 has no tinting or darkening and is completely transparent. In one example, the second shield 32 is a clear polycarbonate lens or shield. The second shield 32 may be referred to as a grinding shield.

With particular reference to FIG. 1, the exemplary headgear 36 is illustrated. Only a portion of and only one side of the headgear 36 is illustrated in FIG. 1, but it should be understood that the headgear 36 is a substantial mirror image about a vertical plane extending through a center of the headgear 36 (and a wearer's head when the headgear is worn). In other words, the headgear 36 is symmetrical on both sides of a wearer's head. The headgear 36 is capable of engaging a wearer's head and supporting the protective headwear 20 on the wearer's head. The headgear 36 may be coupled to the outer shell 24 of the protective headwear 20 in a variety of manners such as, for example, movably coupled, rigidly coupled, unitarily formed with, among other manners.

In the illustrated example, the headgear 36 includes a side plate 64 on each side of the headgear 36, a forehead strap (not shown), a top strap 72, a rear strap 76, an occipital strap 80 and an adjustable member 84 coupled to the occipital strap 80. In one example, the top strap 72 may be pivotally coupled at its ends to respective side plates 64 and may be positioned to extend over a crown or top of a wearer's head. In another example, the top strap 72 may be rigidly or unitarily formed as one-piece with the side plates 64. In one example, the rear strap 76 may be pivotally coupled at its ends to respective side plates 64 and is positioned to extend around a rear of a wearer's head. In another example, the rear strap 76 may be rigidly or unitarily formed as one-piece with side plates 64.

In one example, the occipital strap 80 may be pivotally connected at its ends to the side plates 64, may extend under the side plates 64 (i.e., between the side plates and a wearer's head), may drop down below the rear strap 76, and may wrap around or extend along the occipital crest of a wearer's head, then may extend under the occipital crest. In another example, the occipital strap 80 may be pivotally connected at its ends to the side plates 64, may be positioned externally of the side plates 64 (i.e., the side plates 64 are between ends of the occipital strap 80 and a wearer's head), may drop down below the rear strap 76, and may wrap around or extend along the occipital crest of a wearer's head, then may extend under the occipital crest.

The occipital strap 80 may assist with applying pressure, originating from the protective headwear 20, to be applied to bony structure (e.g., the occipital bone and crest of a skull) of the wearer's head where the wearer has less of a perception of pressure than on soft tissue of the wearer's head.

The illustrated example of the headgear 36 is provided to demonstrate principles of the present disclosure and is not intended to be limiting upon the present disclosure. Rather, the protective headwear 20 may include any type of headgear and all such possibilities are intended to be with in the spirit and scope of the present disclosure.

With continued reference to FIG. 1, the head sleeve 38 is coupled to an interior surface 144 of the outer shell 24 and defines an opening 82 in a bottom thereof to allow a wearer's head to insert into and withdraw from an interior of the head sleeve 38 and an interior 116 of the protective headwear 20. In the illustrated example, the head sleeve 38 includes elastic or other resilient member 83 around the opening 82 to facilitate cinching or compression of the head sleeve around a wearer's neck, thereby closing-off, eliminating or at least reducing the likelihood of air entering into or escaping from the interior 116 of the protective headwear defined by the head sleeve 38 and the outer shell 24. In another example, the head sleeve 38 may include a drawstring around the opening 82 to selectively open and cinch or close the opening 82.

The head sleeve 38 may be coupled to the outer shell 24 in a variety of manners. In one example, the head sleeve 38 is coupled to the interior surface 144 of the outer shell 24 with coupling member 85. In the illustrated example, the coupling member is a hook-and-loop type fastener 85 (see FIG. 1). Alternatively, the head sleeve 38 may be coupled to the interior surface 144 of the outer shell 24 in a variety of other manners including, but not limited to, snaps, screws, detents, buttons, adhesive, bonding, welding, or any other type of permanent, semi-permanent or removable manner, with all of such possibilities intended to be within the spirit and scope of the present disclosure.

The head sleeve 38 cooperates with the outer shell 24 to provide protection to a wearer's head and neck, along with providing an at least partially controlled environment in which the wearer's head is positioned. The controlled environment within the outer shell 24 and head sleeve 38 is at least partially controllable with respect to airflow within the protective headwear 20. The airflow device 40 provides an airflow to the interior 116 of the protective headwear 20 to provide fresh, breathable air for the wearer while also controlling the temperature or at least the perception of temperature on a wearer's head due to convection. The head sleeve 38, outer shell 24, the controlled environment created therein, and the airflow device 40 provide a more comfortable environment within the protective headwear 20 when the protective headwear 20 may be worn in an uncomfortable environment.

Figure 2:
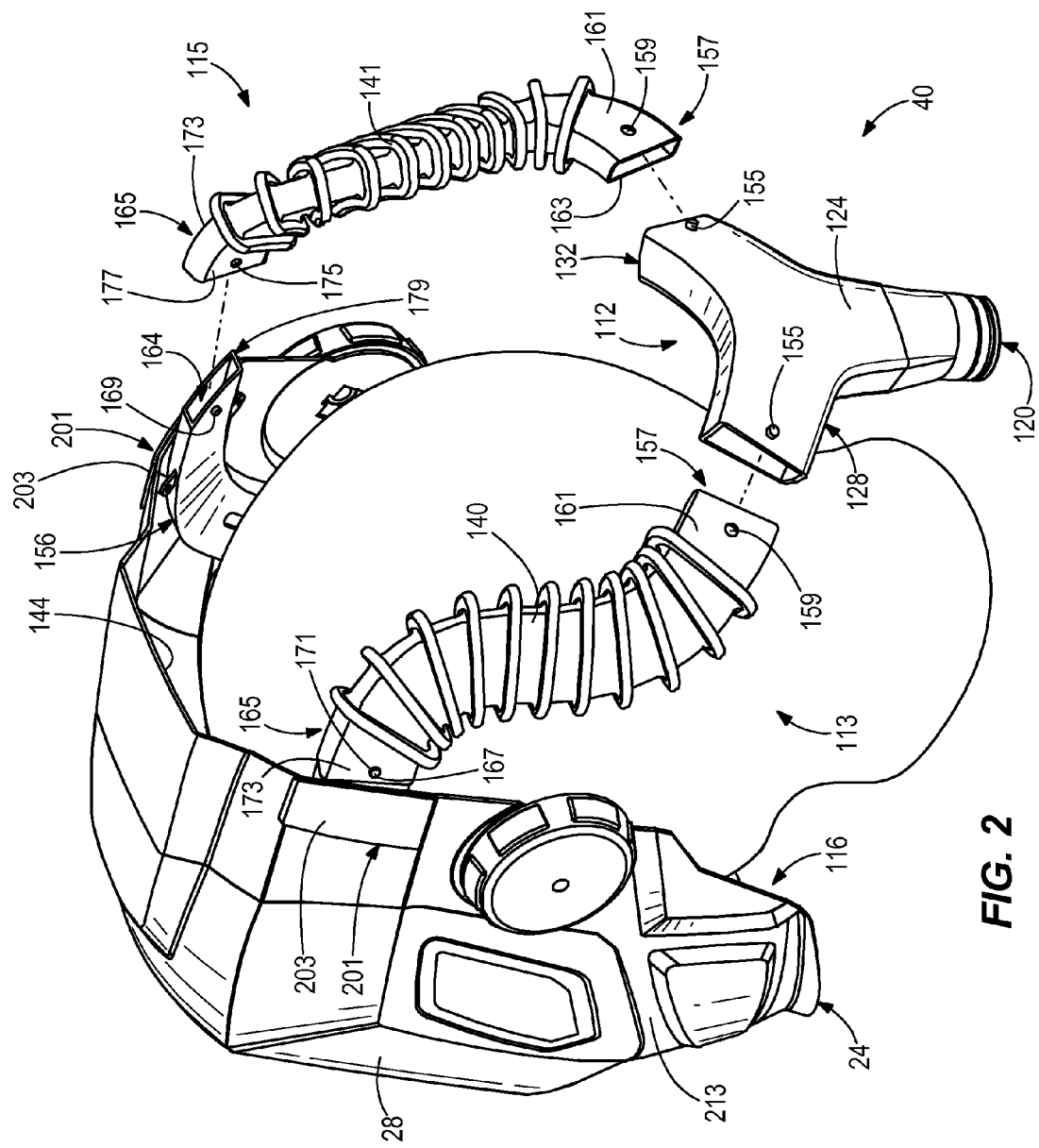
FIG. 2 is a rear, partially exploded perspective view of a portion of the protective headwear and the airflow device shown in FIG. 1, in this view a head sleeve of the protective headwear is removed to facilitate viewing of the interior of the protective headwear, according to one aspect of the present disclosure.
Figure 3:
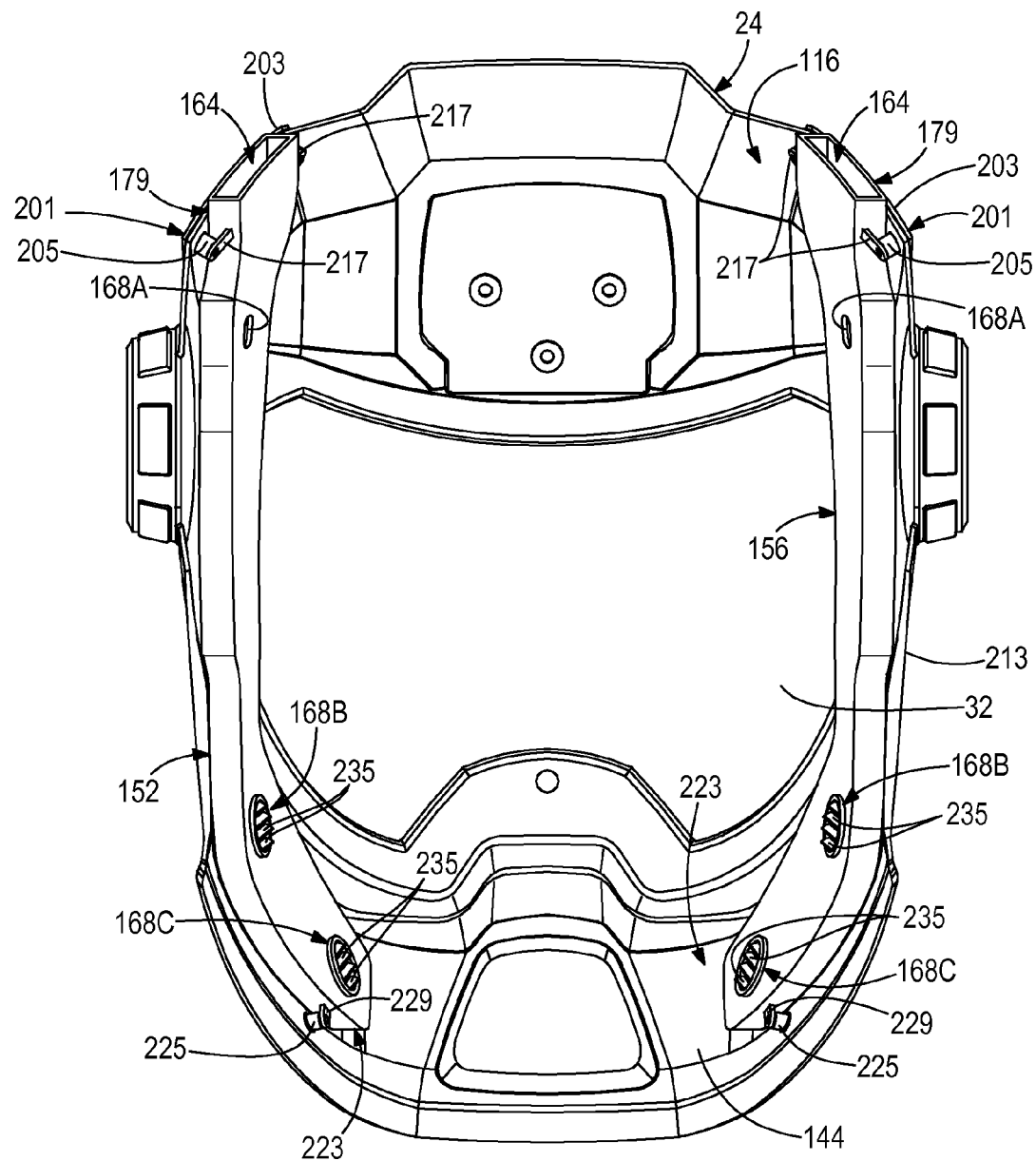
FIG. 3 is a rear view of a portion of the protective headwear shown in FIG. 1, according to one aspect of the present disclosure.
Figure 4:
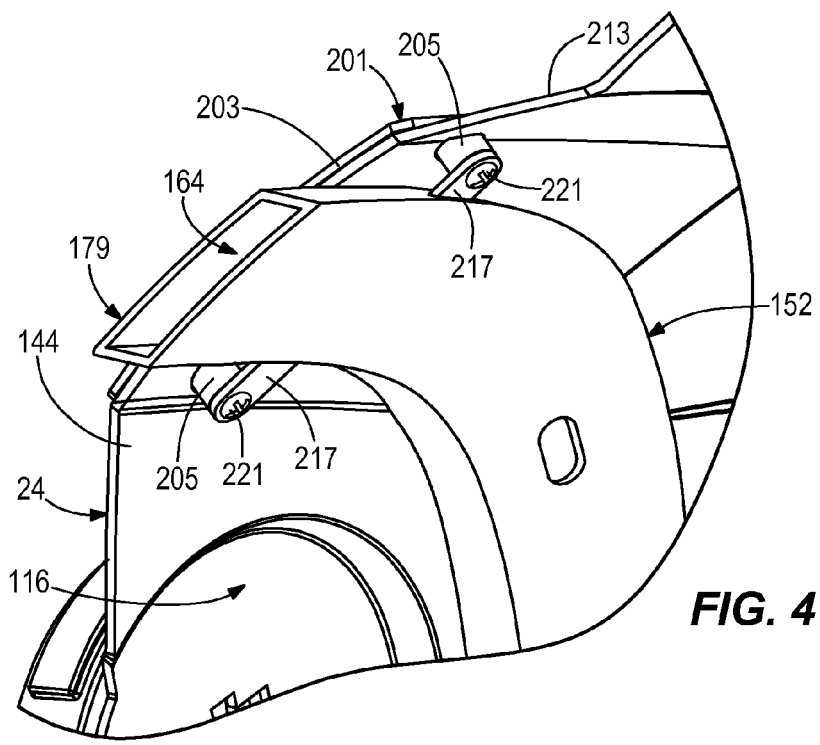
FIG. 4 is a rear perspective view of a portion of the protective headwear shown in FIG. 1, this view shows a portion of the airflow device coupled to a shell of the protective headwear, according to one aspect of the present disclosure.
Figure 5:
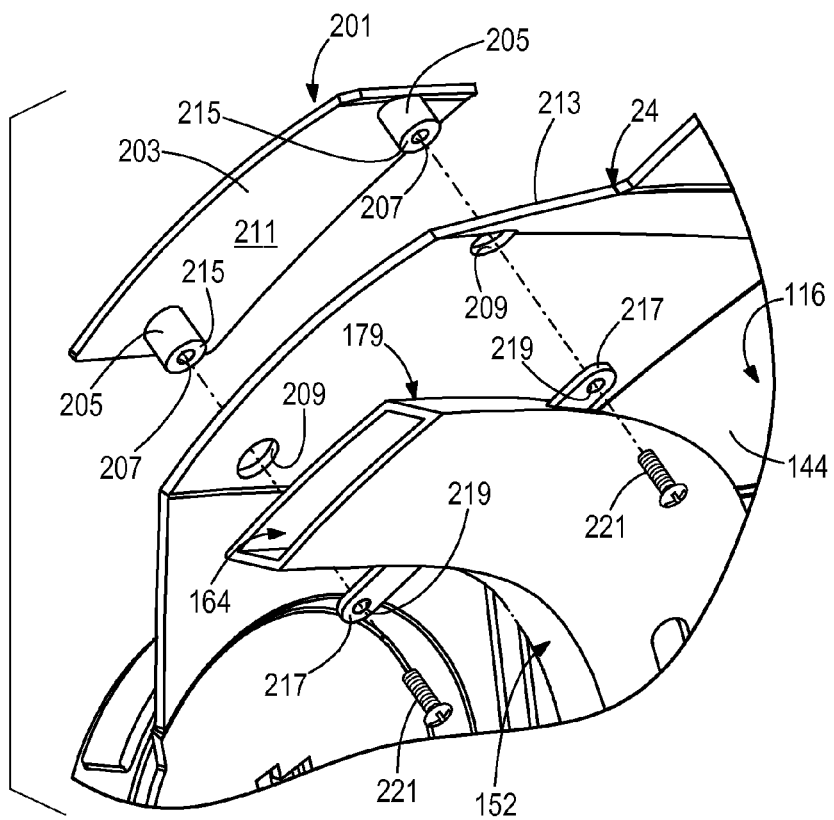
FIG. 5 is an exploded view of the portion of the protective headwear shown in FIG. 4, according to one aspect of the present disclosure.
Figure 6:
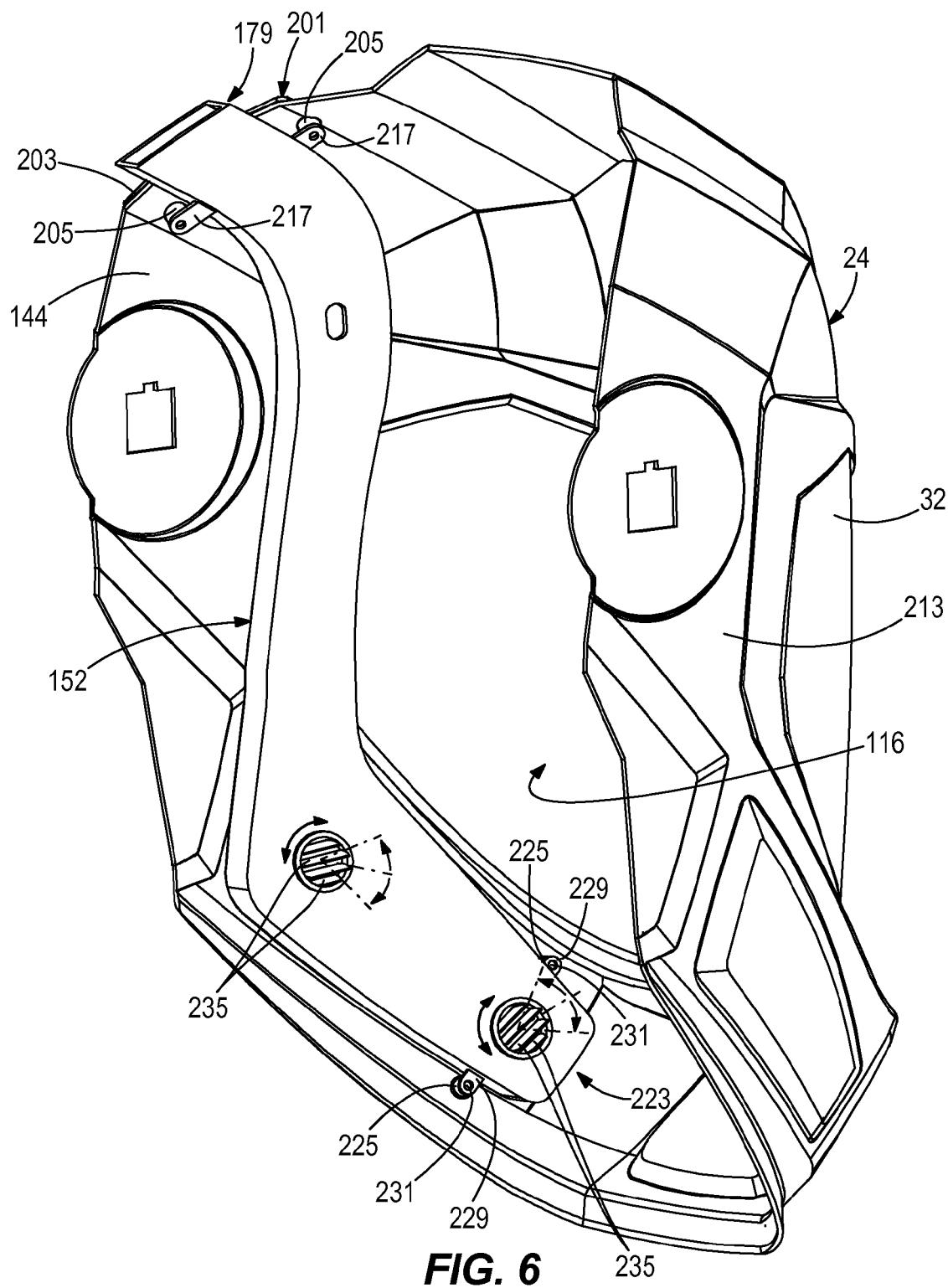
FIG. 6 is a rear perspective view of a portion of the protective headwear shown in FIG. 1, in this view the head sleeve of the protective headwear is removed to expose the interior of the protective headwear and a plurality of air vents in the airflow device, according to one aspect of the present disclosure.

With continued reference to FIGS. 1 and 2, the airflow device 40 includes an air source 100, a blower 104, a hose 108 or other air communication device, a manifold or coupling member 112, and a pair of ducts or tubes 113, 115 extending from the coupling member 112 to a location within the interior 116 of the protective headwear 20. The blower 104 is in fluid communication with the air source 100 and blows air from the air source 100, through the hose 108, and into the coupling member 112, which is coupled to the protective headwear 20 to communicate air from the hose 108 to an interior space 116 within the outer shell 24 of the protective headwear 20. The airflow device 40 may also include one or more filters for filtering the air prior to communication of the air to the interior space 116 of the protective headwear 20.

The coupling member 112 includes an attachment member 120 at an end thereof for coupling the hose 108 to the coupling member 112. The coupling member 112 defines an internal cavity therein for receiving air from the hose 108 and diverting the air downstream to the interior 116 of the protective headwear 20. In the illustrated example, the coupling member 112 includes a "Y" shape comprising a receiving portion 124, a first diversion member 128 and a second diversion member 132 spaced-apart and extending away from the first diversion member 128. The first diversion member 128 and the second diversion member 132 divide the airflow into two streams or portions and communicate the air along two downstream paths into respective first and second ducts 113, 115 and ultimately into different portions of the interior space 116 of the protective headwear 20.

The first diversion member 128 is coupled to the first duct 113 and the second diversion member 132 is coupled to the second duct 115. The first duct 113 is positioned along a first side of a wearer's head and the second duct 115 is positioned along a second side of the wearer's head opposite the first side.

In the illustrated example, the first duct 113 includes a first flexible portion or duct 140 and a first shell portion or duct 152, and the second duct 115 includes a second flexible portion or duct 141 and a second shell portion or duct 156. The first and second flexible portions 140, 141 are respectively coupled to the first and second diversion members 128, 132. The first and second flexible portions 140, 141 may be coupled to the first and second diversion members 128, 132 in a variety of manners and all manners are intended to be within the spirit and scope of the present disclosure. In the illustrated example, each of the first and second diversion members 128, 132 includes a first projection 155 extending from a first or external side of the first and second diversion members 128, 132 and a second projection extending from a second or internal side of the first and second diversion members 128, 132 opposite the first side. Each of first ends 157 of the first and second flexible portions 140, 141 define a first aperture 159 in a first or external side 161 thereof and a second aperture in a second or interior side 163 thereof. The apertures 159 are complementary sized and shaped to the projections 155 to accommodate insertion of the projections 155 into the apertures 159, thereby coupling the first ends 157 of the first and second flexible portions 140, 141 to the manifold or coupling member 112. In other examples, each of the first and second diversion members 128, 132 may include only a single projection and the first ends 157 of the first and second flexible portions 140, 141 may include only a single aperture to couple the flexible portions 140, 141 to the manifold or coupling member 112. In further examples, the first and second flexible portions 140, 141 may include one or more projections and the coupling member may include one or more complementary apertures for coupling the first and second flexible portions 140, 141 to the coupling member 112. In still other examples, the first ends 157 of the flexible portions 140, 141 may be additionally coupled to the manifold or coupling member 112 with adhesive.

Second ends 165 of the first and second flexible portions 140, 141 are respectively coupled to the first and second shell portions 152, 156 in similar manners to the illustrated example of the manner in which the first ends 157 of the first and second flexible portions 140, 141 are coupled to the manifold or coupling member 112. In the illustrated example, each of the first and second shell portions 152, 156 includes a first projection 167 extending from a first or external side of the first and second shell portions 152, 156 and a second projection 169 extending from a second or internal side of the first and second shell members 152, 156 opposite the first side. Each of second ends 165 of the first and second flexible portions 140, 141 define a first aperture 171 in a first or external side 173 thereof and a second aperture 175 in a second or interior side 177 thereof. The apertures 171, 175 are complementary sized and shaped to the projections 167, 169 to accommodate insertion of the projections 167, 169 into the apertures 171, 175, thereby coupling the second ends 165 of the first and second flexible portions 140, 141 to the first and second shell portions 152, 156. In other examples, each of the first and second shell portions 152, 156 may include only a single projection and the second ends 165 of the first and second flexible portions 140, 141 may include only a single aperture to couple the flexible portions 140, 141 to the first and second shell portions 152, 156. In further examples, the first and second flexible portions 140, 141 may include one or more projections and the first and second shell portions 152, 156 may include one or more complementary apertures for coupling the first and second flexible portions 140, 141 to the first and second shell portions 152, 156. In still other examples, the second ends 165 of the flexible portions 140, 141 may be additionally coupled to the first and second shell portions 152, 156 with adhesive.

With reference to FIGS. 1-4, ends 179 of the first and second shell portions 152, 156 are positioned externally, outside, behind or beyond an outermost edge of the outer shell 24. Also, in the illustrated example, the first and second flexible portions 140, 141 are coupled to ends 179 of the first and second shell portions externally, outside, behind or beyond an outermost edge of the outer shell 24. In the illustrated example, the head sleeve 38 defines a pair of apertures or openings 181 through which the ends 179 of the first and second shell portions extend to facilitate the first and second ducts 113, 115 from passing from an exterior of the outer shell 24, through the head sleeve 38, and to the interior 116 of the protective headwear 20.

The flexible portions 140, 141 allow the first and second ducts 113, 115 to be adjusted to accommodate movement of the outer shell 24 relative to the headgear 36 between a downward operating position and an upward inoperative position, heads of different sizes and shapes, different types of headgear, or other reasons. In some examples, the first and second ducts 113, 115 may not include a flexible portion and, instead, the first and second ducts 113, 115 may be completely rigid and extend from the manifold or coupling member 112 to their termination location within the outer shell 24.

In the illustrated example, the airflow device 40 is not coupled to the headgear 36 and the coupling member 112 is positioned to a rear and rests at a rear of a wearer's head (see FIG. 1) either spaced-apart from the headgear 36 and the wearer's head or against at least one of the headgear 36 and a rear of the wearer's head. In another example, the airflow device 40 is coupled to the headgear 36 for additional support by the coupling member 112 being coupled to the headgear 36 at a rear of the headgear and rear of a wearer's head. In one example, an attachment member couples the coupling member 112 to the rear strap 76 of the headgear 36. The attachment member may be a strap or other type of attachment members. In other examples, the coupling member 112 may be coupled to the top strap 72, the occipital strap 80, or the side plate 64. In still other examples, the coupling member 112 may be coupled to any combination of the top strap 72, the rear strap 76, the occipital strap 80 and the side plate 64. In further examples, any portion(s) of the airflow device 40 may be coupled to any portion of the headgear 36. It should be understood that the airflow device 40 may or may not be coupled to any other portion of the protective headwear 20 and all of such possibilities are intended to be within the spirit and scope of the present disclosure.

Referring now to FIGS. 1-7, the first shell portion 152 is coupled to and in fluid communication with the first flexible portion 140 to receive air from the coupling member 112 and the second shell portion 156 is coupled to and in fluid communication with the second flexible portion 141 to receive air from the coupling member 112.

The first and second shell portions 152, 156 are similar in shape and configuration and it should be understood that the second shell portion 156 is a substantial mirror image of the first shell portion 152. In other words, in the illustrated example, the protective headwear 20 is symmetrical on both sides of a wearer's head. In another example, the protective headwear 20 may not be symmetrical on both sides and the first and second shell portions 152, 156 may not be substantially identical in shape and configuration. In a further example, the protective headwear 20 may include only one shell portion on only one side of the protective headwear 20. In such an example, the coupling member 112 may only include a single diversion member (or no diversion member because it may not be necessary to divert the air flow) coupled to and in fluid communication with the single shell portion. In still another example, the protective headwear 20 may include more than two shell portions. In such an example, the coupling member 112 may include a complementary number of diversion members to couple to and be in fluid communication with the plurality of shell portions included in the protective headwear 20. Additionally, in such an example, the first and second ducts 113, 115 may include a complimentary number of flexible portions to couple the manifold or coupling member 112 to the shell portions.

Returning to the illustrated example and to FIGS. 1-7, the first and second shell portions 152, 156 are coupled to the outer shell 24. The first and second shell portions 152, 156 may be coupled to the outer shell 24 in a variety of manners and all possibilities are intended to be within the spirit and scope of the present disclosure. For example, the first and second shell portions 152, 156 may be coupled to the outer shell by fastening, bonding, welding, unitarily forming as one-piece with, friction-fit, interference-fit, tongue and groove, detent, snap-fit, hook and loop type fastening, or any other manner of permanently, semi-permanently, or removably coupling.

In the illustrated example, the first and second shell portions 152, 156 are coupled to outer shell in similar manners and, therefore, only coupling of the first shell portion 152 will be described with it being understood that the description may apply mutatis mutandis to coupling the second shell portion 156 to the outer shell 24. In other examples, the first and second shell portions 152, 156 may be coupled to the outer shell 24 in different manners.

With reference to FIGS. 1-7, the protective headwear 20 includes a coupling member 201 including a base 203 and a pair of projections 205 extending from the base 203. An aperture 207 is defined in each of the projections 205. The outer shell 24 defines a pair of apertures 209 defined therein configured to respectively receive the projections 205. With the projections 205 inserted into the apertures 209 and an interior surface 211 of the base 203 engaging an outer surface 213 of the outer shell 24, ends 215 of the projections 205 are positioned in the interior 116 of the outer shell 24. The first shell portion 152 includes a pair of flanges 217, each of which defines an aperture 219 therein. The flanges 217 engage ends 215 of the projections 205 and apertures 219 of the flanges 217 align with apertures 207 in the projections. Fasteners 221 are inserted (e.g., threaded in the illustrated example) into the aligned apertures 207, 219 to couple the first shell portion 152 to the outer shell 24. The first shell portion 152 is also coupled to the outer shell 24 near a second end 223 of the first shell portion 152. A pair of projections 225 extend from the interior surface 144 of the outer shell 24 and each projection 225 defines an aperture therein. The first shell portion 152 includes a pair of flanges 229, each of which defines an aperture 231 therein. The flanges 229 engage the projections 225 and apertures 231 of the flanges 229 align with apertures in the projections 225. Fasteners are inserted (e.g., threaded fasteners) into the aligned apertures to couple the first shell portion 152 to the outer shell 24 near the second end 223 of the first shell portion 152.

Figure 7:
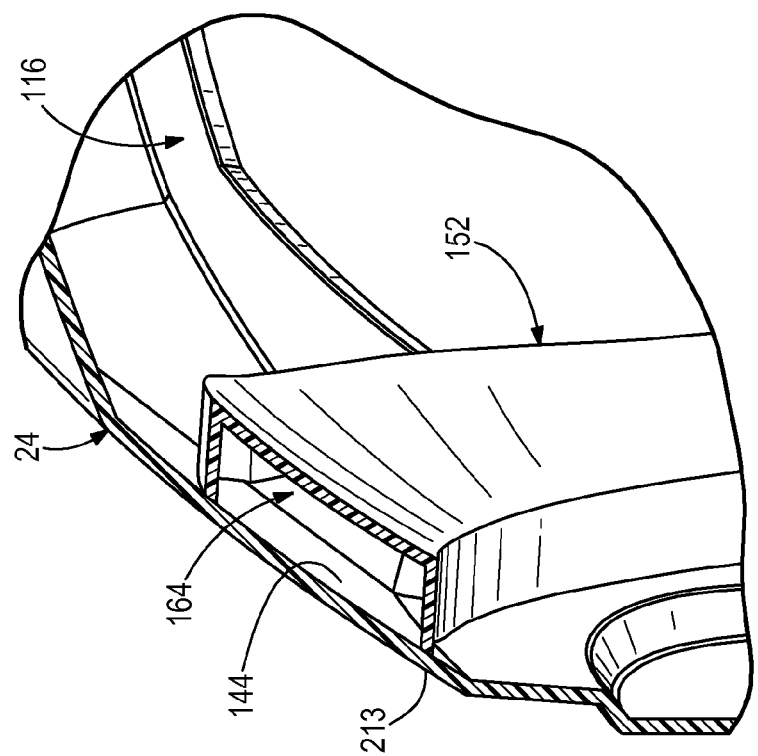
FIG. 7 is a cross-sectional view taken along line 7-7 in FIG. 1, according to one aspect of the present disclosure.
Figure 8:
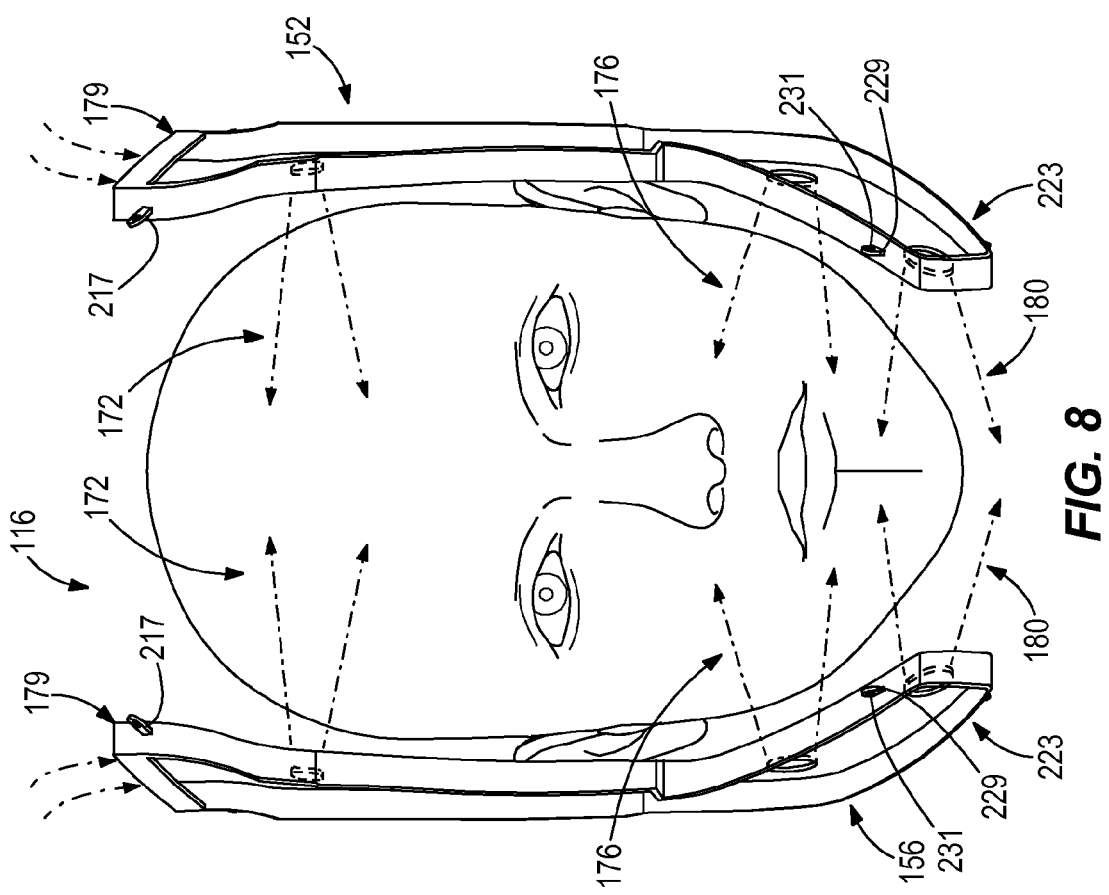
FIG. 8 is a front view of a portion of the airflow device shown in FIG. 1 with one example of an environment with which the airflow device may be associated, this view shows the airflow device directing airflow on a wearer's face without directing the airflow into the wearer's eyes, according to one aspect of the present disclosure.

With particular reference to FIG. 7, an airflow path or duct cavity 164 is defined along each of two sides of the interior surface 144 of the outer shell 24 (right side and left side of interior surface of the outer shell) by a combination of the first and second shell portions 152, 156 and the interior surface 144 of the outer shell 24. Three sides of each duct cavity 164 is defined by the respective first or second shell portion 152, 156 and a fourth side of each duct cavity 164 is defined by the interior surface 144 of the outer shell 24.

Referring now to FIGS. 1, 3, 4, 6 and 8, each of the first and second shell portions 152, 156 includes a plurality of exhaust ports 168 configured to exhaust air from the first and second shell portions 152, 156 to the interior space 116 of the protective headwear 20. In the illustrated example, each helmet duct 152, 156 includes three exhaust ports 168A, 168B, 168C. Alternatively, the shell portions 152, 156 may include any quantity of exhaust ports and be within the spirit and scope of the present disclosure. In the illustrated example, exhaust port 168A has a different shape than exhaust ports 168B, 168C. In this illustrated example, exhaust port 168A is generally oval in shape and exhaust ports 168B, 168C are generally round in shape. It should be understood that the exhaust ports may have any shape, may be different in shape relative to each other in any combination, or and may all be similar in shape, and all of such possibilities are intended to be within the spirit and shape of the present disclosure. Returning to the illustrated example, exhaust ports 168B, 168C are independently adjustable to selectively alter a directional flow of the air exhausting from the exhaust ports 168B, 168C and exhaust port 168A is fixed and not adjustable. It should be understood that any number of the exhaust ports 168 may be adjustable, rigid and non-adjustable, and any combination thereof and all of such possibilities are intended to be within the spirit and scope of the present disclosure.

In one example, the adjustable exhaust ports 168 have adjustability along multiple axes. In another example, the adjustable exhaust ports 168 have adjustability along two axes. In a further example, the adjustable exhaust ports 168 have adjustability along three axes. The illustrated example provides adjustable exhaust ports 168B, 168C adjustable along three axes. The direction of the exhaust ports 168 may be adjusted to accommodate varying sizes and shapes of wearers' faces, variance in environments in which the protective headwear 20 may be used, and accommodate wearer's preferences with respect to where and how they desire airflow to impact their face.

Additionally, with respect to the illustrated example, the adjustable exhaust ports 168B, 168C include dampers 235 for adjusting a quantity of airflow passing there through. The dampers are adjustable to a variety of positions between and including a fully opened position, in which the dampers allow the most airflow to pass there through, and a fully closed position, in which the dampers prevent any airflow from passing there through. Any number of the exhaust ports 168 may include dampers (including zero and all of the ports) and all of such possibilities are intended to be within the spirit and scope of the present disclosure.

Figure 9:
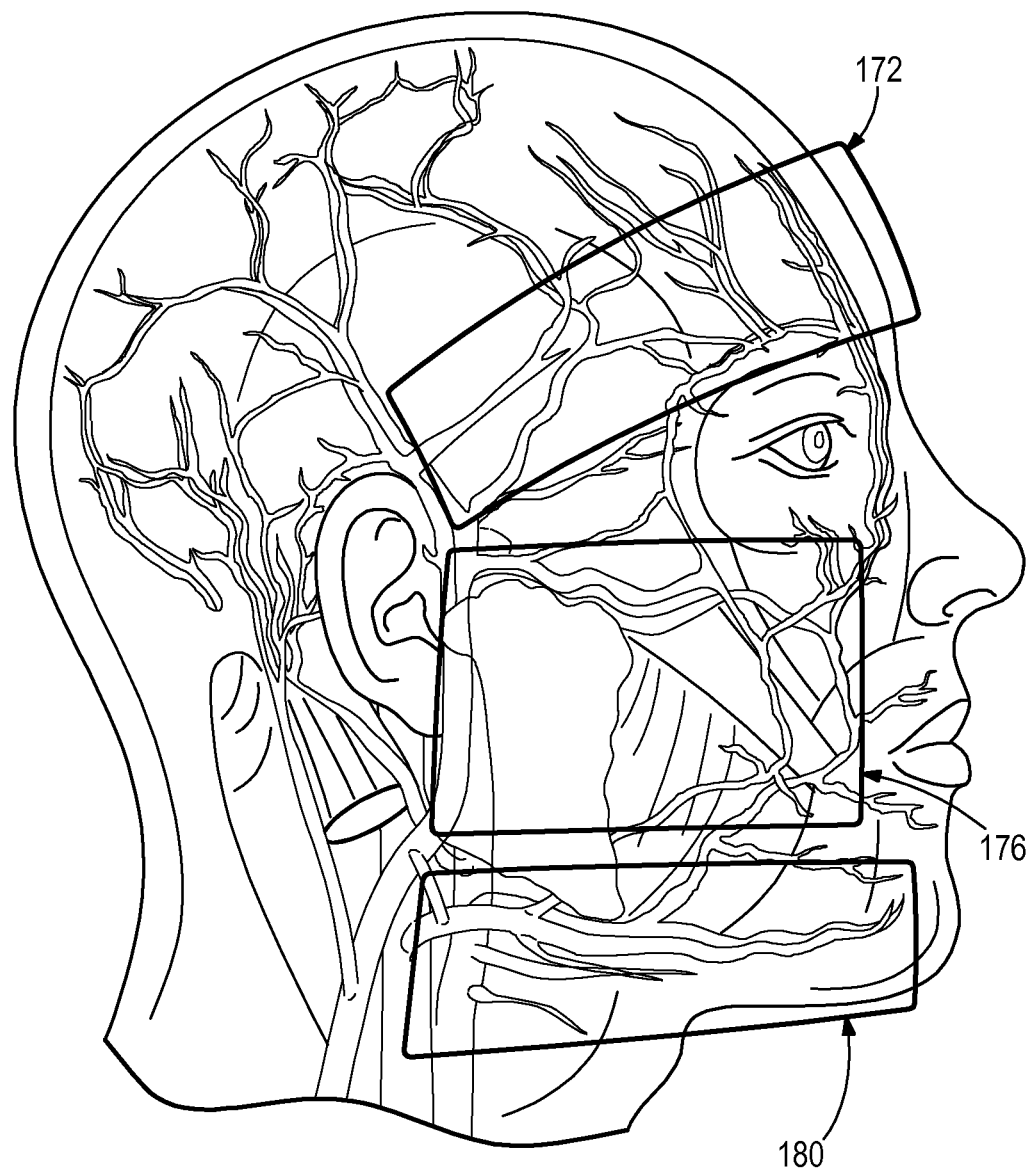
FIG. 9 is a diagram of another example of an environment with which the airflow device may be associated, according to one aspect of the present disclosure.

With continued reference to FIGS. 1, 3, 4, 6 and 8 and additional reference to FIG. 9, the exhaust ports 168 are positioned along the first and second shell portions 152, 156 to supply air to particular portions of the wearer's head. In the illustrated example, top exhaust ports 168A supply air to first zones 172 (one on each side of the wearer's head), middle exhaust ports 168B supply air to second zones 176 (one on each side of the wearer's head), and bottom exhaust ports 168C supply air to third zones 180 (one on each side of the wearer's head). In one example, the first zones 172 generally correspond to temples and/or a forehead of the wearer's head, second zones 176 generally correspond to cheeks of the wearer's head, and third zones 180 generally correspond to jaw and/or neck areas of the wearer's head. In other examples, the zones may correspond to other portions of a wearer's head.

In the illustrated example, the exhaust ports 168 may be positioned to exhaust air generally perpendicular to the portions or zones of the wearer's head associated with the exhaust ports 168. Exhausting air at an angle generally perpendicular to the associated portion of the wearer's head generates more turbulence (compared to a laminar exhaust stream when air is delivered parallel or generally parallel to a portion of the wearer's head) when the exhaust stream engages the portion of the wearer's head.

In one example, the zones or portions of the wearer's head may be determined based on those areas of a wearer's head that have a higher perception of airflow and cooling. For example, a human face has certain areas with large concentrations of superficial blood vessels such as temples, forehead, cheeks, jaw and neck. Additionally, it is important to avoid blowing air directly into a wearer's eyes in order to avoid drying a wearer's eyes or otherwise deteriorating a wearer's comfort level. Moreover, exhausting airflow in the manner performed by the present disclosure may blow air onto a larger percentage of the wearer's face than conventional airflow, which is blown from a location above the wearer's forehead straight down over the wearer's face and into the wearer's eyes.

In some examples, a velocity and/or an angle at which air exhausts from the exhaust ports 168 may be adjusted. For example, the position and/or exhaust apertures associated with the exhaust ports 168 or the exhaust ports 168 themselves may be adjusted to adjust the exhaust velocity and/or direction of the air (as described above), the coupling member 112 may include an actuator and/or damper that may be actuated to adjust the exhaust velocity and/or angle of the air, the blower 104 may be adjusted to adjust the exhaust velocity and/or angle of the air, or any of a wide variety of other manners of adjusting air velocity and/or air angle are possible, and all of such possibilities are intended to be within the spirit and scope of the present disclosure.

The components of the present disclosure utilized to communicate air to an interior space 116 of the protective headwear 20 are coupled and positioned relative to the protective headwear 20 to locate a center of gravity in a more ideal location relative to a wearer's head, thereby decreasing the level of stress and pressure applied to a wearer's head. For example, the manifold or coupling member 112 is positioned near or to a rear of the protective headwear 20 behind a wearer's head, thereby adding weight to a rear of the protective headwear behind a wearer's head and biasing the center of gravity in a rearward direction. Positioning weight behind a wearer's head via the manifold and portions of the first and second ducts 113, 115 offsets weight in front of the wearer's head provided by the outer shell 24 and shields 28, 32. During welding or other operating process, a wearer may be looking forward and downward, thereby shifting the center of gravity forward of a middle of the wearer's head. By locating the coupling member 112 at a rear of the protective headwear 20, the coupling member 112 and other air communication components contribute to positioning the center of gravity more towards a rear of the protective headwear 20 than it would otherwise be without the coupling member 112 and other air components being positioned where they are. Additionally, the first and second shell portions 152, 156 are minimal in size, weight and profile, and are appropriately positioned to contribute to a more ideal location of the center of gravity. In some examples, a more ideal location of the center of gravity of the protective headwear 20 is over a middle or mid-line of the wearer's head, thereby decreasing any unnecessary torque applied to a wearer's head and neck by having the center of gravity located toward a front or a rear of the protective headwear 20. Furthermore, extending one helmet duct along each side of the protective headwear 20 (compared to a single large duct over a top of a wearer's head) requires less material, thereby reducing the overall weight of the protective headwear 20. A net effect of the components associated with providing airflow to an interior 116 of the protective headwear 20 will be to position the center of gravity closer to a mid-line of the wearer's head.

It should be understood that the above examples of the protective headwear and the airflow device are provided for exemplary purpose to demonstrate at least some of the principles of the present disclosure. Other variants, embodiments, and examples are possible and all of which are intended to be within the spirit and scope of the present disclosure. For example, the protective headwear may be any type of protective headwear and the airflow device may be coupled to any type of protective headwear including, but not limited to, hard hats, bicycle helmets, military helmets, or any other type of protective headwear. Also, for example, the coupling member may include a single duct that couples with a helmet duct, and the helmet duct may divert into multiple helmet ducts to communicate airflow to various locations within the interior of the protective headwear. Further, for example, the coupling member and other components of the airflow device may be coupled to any portion of the protective headwear, not just the headgear. Still further, for example, the airflow device may include any number and type of components to communicate fluid from the air source to the interior of the protective headwear. Additionally, for example, the coupling member may be included as part of the protective headwear by either coupling or unitarily forming the coupling member with the remainder of the protective headwear. Further yet, for example, the manifold or coupling member may divert the airflow into two ducts and the two ducts may extend from the manifold or coupling member all the way to a location where the ducts terminate within the interior of the protective headwear. That is, in this example, the airflow device may be characterized to include only two ducts and the ducts may not be parsed to include various portions as described in the above example. Moreover, it should be understood that the present disclosure is intended to include any number of ducts, tubes, etc., between the manifold or coupling member and a final termination location for conveying air from the manifold or coupling member to the final destination.

It should be understood that the use of any orientation or directional terms herein such as, for example, "top", "bottom", "front", "rear", "back", "left", "right", "side", etc., is not intended to imply only a single orientation of the item with which it is associated or to limit the present disclosure in any manner. The use of such orientation or directional terms is intended to assist with the understanding of principles disclosed herein and to correspond to the exemplary orientation illustrated in the drawings. For example, the protective headwear and airflow device may be utilized in any orientation and use of such terms is intended to correspond to the exemplary orientation of the protective headwear and airflow device illustrated in the drawings. The use of these terms in association with the protective headwear and airflow device is not intended to limit the protective headwear and airflow device to a single orientation or to limit the protective headwear and airflow device in any manner.

The Abstract of the disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A protective headwear comprising:
an outer shell;
a first shell duct coupled to the outer shell and including a first exhaust port;
a second shell duct coupled to the outer shell and spaced apart from the first shell duct, wherein the second shell duct includes a second exhaust port; and
a manifold positioned externally of the outer shell and configured to divert airflow into at least a first portion of airflow and a second portion of airflow, the manifold including
a first diversion member coupled to and in fluid communication with the first shell duct to provide the first portion of airflow to the first shell duct, wherein the first diversion member is positioned externally of the outer shell, and
a second diversion member coupled to and in fluid communication with the second shell duct to provide the second portion of airflow to the second shell duct, wherein the second diversion member is positioned externally of the outer shell;
wherein the first exhaust port of the first shell duct is one of a first plurality of exhaust ports, and wherein the second exhaust port of the second shell duct is one of a second plurality of exhaust ports;
wherein at least one of the first plurality of exhaust ports of the first shell duct is adjustable to adjust at least one of airflow direction and airflow volume exhaustible from the at least one of the first plurality of exhaust ports of the first shell duct, and wherein at least one of the second plurality of exhaust ports of the second shell duct is adjustable to adjust at least one of airflow direction and airflow volume exhaustible from the at least one of the second plurality of exhaust ports of the second shell duct;
wherein the at least one of the first plurality of exhaust ports of the first shell duct that is adjustable is rotatable to adjust air flow direction and includes a damper for adjusting airflow volume exhaustible from the at least one of the first plurality of exhaust ports of the first shell duct, and wherein the at least one of the second plurality of exhaust ports of the second shell duct that is adjustable is rotatable to adjust air flow direction and includes a damper for adjusting airflow volume exhaustible from the at least one of the second plurality of exhaust ports of the second shell duct.

2. The protective headwear of claim 1, wherein one of the first plurality of exhaust ports of the first shell duct is positioned in a top half of the outer shell and another one of the first plurality of exhaust ports of the first shell duct is positioned in a bottom half of the outer shell, and wherein one of the second plurality of exhaust ports of the second shell duct is positioned in a top half of the outer shell and another one of the second plurality of exhaust ports of the second shell duct is positioned in a bottom half of the outer shell.

3. The protective headwear of claim 1, wherein at least two of the first plurality of exhaust ports of the first shell duct are adjustable to adjust at least one of airflow direction and airflow volume exhaustible from the at least two of the first plurality of exhaust ports, and wherein at least two of the second plurality of exhaust ports of the second shell duct are adjustable to adjust at least one of airflow direction and airflow volume exhaustible from the at least two of the second plurality of exhaust ports.

4. The protective headwear of claim 1, wherein one of the first plurality of exhaust ports of the first shell duct is configured to exhaust air onto a forehead of a wearer and another of the first plurality of exhaust ports of the first shell duct is configured to exhaust air onto a chin of the wearer, and wherein one of the second plurality of exhaust ports of the second shell duct is configured to exhaust air onto the forehead of the wearer and another of the second plurality of exhaust ports of the second shell duct is configured to exhaust air onto the chin of the wearer.

5. The protective headwear of claim 1, wherein at least one of the first plurality of exhaust ports is positioned in a bottom half of the outer shell, and wherein at least one of the second plurality of exhaust ports is positioned in the bottom half of the outer shell.

6. The protective headwear of claim 1, wherein the protective headwear is a welding helmet.

7. The protective headwear of claim 1, further comprising:
a first flexible duct coupled to and between the first shell duct and the first diversion member to provide the first portion of airflow from the first diversion member to the first shell duct; and
a second flexible duct coupled to and between the second shell duct and the second diversion member to provide the second portion of airflow from the second diversion member to the second shell duct.

8. The protective headwear of claim 7, wherein one of a first end of the first flexible duct and an end of the first diversion member includes a projection and the other one of the first end of the first flexible duct and the end of the first diversion member includes an aperture, wherein the projection is at least partially received in the aperture to couple the first flexible duct to the first diversion member; and
wherein one of a second end of the first flexible duct and an end of the first shell duct includes a projection and the other one of the second end of the first flexible duct and the end of the first shell duct includes an aperture, wherein the projection is at least partially received in the aperture to couple the first flexible duct to the first shell duct.

9. The protective headwear of claim 1, wherein the first shell duct is offset to a first side of a plane extending through a center of the outer shell from a front to a rear of the outer shell, and wherein the second shell duct is offset to a second side of the plane.

10. A protective headwear comprising:
an outer shell;
a first shell duct coupled to the outer shell and including a first exhaust port;
a second shell duct coupled to the outer shell and spaced apart from the first shell duct, wherein the second shell duct includes a second exhaust port; and
a manifold positioned externally of the outer shell and configured to divert airflow into at least a first portion of airflow and a second portion of airflow, the manifold including
a first diversion member coupled to and in fluid communication with the first shell duct to provide the first portion of airflow to the first shell duct, wherein the first diversion member is positioned externally of the outer shell, and
a second diversion member coupled to and in fluid communication with the second shell duct to provide the second portion of airflow to the second shell duct, wherein the second diversion member is positioned externally of the outer shell;
wherein the first exhaust port of the first shell duct is one of a first plurality of exhaust ports, and wherein the second exhaust port of the second shell duct is one of a second plurality of exhaust ports;
wherein at least one of the first plurality of exhaust ports of the first shell duct is adjustable to adjust at least one of airflow direction and airflow volume exhaustible from the at least one of the first plurality of exhaust ports of the first shell duct, and wherein at least one of the second plurality of exhaust ports of the second shell duct is adjustable to adjust at least one of airflow direction and airflow volume exhaustible from the at least one of the second plurality of exhaust ports of the second shell duct;
wherein the at least one of the first plurality of exhaust ports of the first shell duct that is adjustable adjusts both airflow direction and airflow volume exhaustible from the at least one of the first plurality of exhaust ports of the first shell duct, and wherein the at least one of the second plurality of exhaust ports of the second shell duct that is adjustable adjusts both airflow direction and airflow volume exhaustible from the at least one of the second plurality of exhaust ports of the second shell duct.

11. The protective headwear of claim 10, wherein one of the first plurality of exhaust ports of the first shell duct is positioned in a top half of the outer shell and another one of the first plurality of exhaust ports of the first shell duct is positioned in a bottom half of the outer shell, and wherein one of the second plurality of exhaust ports of the second shell duct is positioned in a top half of the outer shell and another one of the second plurality of exhaust ports of the second shell duct is positioned in a bottom half of the outer shell.

12. The protective headwear of claim 10, wherein at least two of the first plurality of exhaust ports of the first shell duct are adjustable to adjust at least one of airflow direction and airflow volume exhaustible from the at least two of the first plurality of exhaust ports, and wherein at least two of the second plurality of exhaust ports of the second shell duct are adjustable to adjust at least one of airflow direction and airflow volume exhaustible from the at least two of the second plurality of exhaust ports.

13. The protective headwear of claim 10, wherein one of the first plurality of exhaust ports of the first shell duct is configured to exhaust air onto a forehead of a wearer and another of the first plurality of exhaust ports of the first shell duct is configured to exhaust air onto a chin of the wearer, and wherein one of the second plurality of exhaust ports of the second shell duct is configured to exhaust air onto the forehead of the wearer and another of the second plurality of exhaust ports of the second shell duct is configured to exhaust air onto the chin of the wearer.

14. The protective headwear of claim 10, wherein at least one of the first plurality of exhaust ports is positioned in a bottom half of the outer shell, and wherein at least one of the second plurality of exhaust ports is positioned in the bottom half of the outer shell.

15. The protective headwear of claim 10, wherein the protective headwear is a welding helmet.

16. The protective headwear of claim 10, further comprising:
    a first flexible duct coupled to and between the first shell duct and the first diversion member to provide the first portion of airflow from the first diversion member to the first shell duct; and
    a second flexible duct coupled to and between the second shell duct and the second diversion member to provide the second portion of airflow from the second diversion member to the second shell duct.

17. The protective headwear of claim 16, wherein one of a first end of the first flexible duct and an end of the first diversion member includes a projection and the other one of the first end of the first flexible duct and the end of the first diversion member includes an aperture, wherein the projection is at least partially received in the aperture to couple the first flexible duct to the first diversion member; and
    wherein one of a second end of the first flexible duct and an end of the first shell duct includes a projection and the other one of the second end of the first flexible duct and the end of the first shell duct includes an aperture, wherein the projection is at least partially received in the aperture to couple the first flexible duct to the first shell duct.

18. The protective headwear of claim 10, wherein the first shell duct is offset to a first side of a plane extending through a center of the outer shell from a front to a rear of the outer shell, and wherein the second shell duct is offset to a second side of the plane.

* * * * *